United States Patent [19]

Matsumoto et al.

[11] Patent Number: 5,091,569
[45] Date of Patent: Feb. 25, 1992

[54] DI-TERT-BUTYL(HYDROXY)PHENYLTHIO SUBSTITUTED HYDROXAMIC ACID DERIVATIVES

[75] Inventors: Saichi Matsumoto, Osaka, Japan; Takuji Mizui, San Francisco, Calif.; Masami Doteuchi, Osaka, Japan

[73] Assignee: Shionogi & Co., Ltd., Osaka, Japan

[21] Appl. No.: 540,625

[22] Filed: Jun. 19, 1990

[30] Foreign Application Priority Data

Jun. 29, 1989 [JP] Japan .................. 1-167497

[51] Int. Cl.$^5$ .................. C07C 259/06; A61K 31/165; A61K 31/185
[52] U.S. Cl. .................................................. 562/621
[58] Field of Search .......................................... 562/621

[56] References Cited

U.S. PATENT DOCUMENTS

| | | | |
|---|---|---|---|
| 4,029,812 | 6/1977 | Wagner et al. | 424/298 |
| 4,076,841 | 2/1978 | Wagner et al. | 424/324 |
| 4,078,084 | 3/1978 | Wagner et al. | 424/324 |
| 4,605,669 | 8/1986 | Summers, Jr. | 514/575 |
| 4,608,390 | 8/1986 | Summers, Jr. | 514/575 |
| 4,623,661 | 11/1986 | Summers, Jr. | 514/575 |
| 4,738,986 | 4/1988 | Kheen et al. | 514/575 |
| 4,857,558 | 8/1989 | Mueller | 514/712 |
| 4,861,798 | 8/1989 | Tramposch et al. | 514/575 |
| 4,873,259 | 10/1989 | Summers, Jr. et al. | 514/443 |
| 4,897,422 | 1/1990 | Summers, Jr. | 514/575 |

FOREIGN PATENT DOCUMENTS 0190682 8/1986 European Pat. Off. .
0301861 2/1989 European Pat. Off. .
2212153 7/1989 United Kingdom .

Primary Examiner—J. E. Evans
Attorney, Agent, or Firm—Wenderoth, Lind & Ponack

[57] ABSTRACT

(Di-tert-butylhydroxyphenyl)thio substituted hydroxamic acid derivatives of the formula:

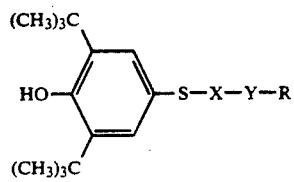

wherein X is straight or branched $C_1$ to $C_{15}$ alkylene which may be attached to Y through phenylene, provided that X is not n-butylmethylene; Y is CO—N(OH) or N(OH)—CO; and R is hydrogen or straight or branched $C_1$ to $C_9$ alkyl, $C_3$ to $C_9$ cycloalkyl, aryl, or aralkyl, provided that R is not hydrogen when Y—R is N(OH)—CO—R; or a pharmaceutically acceptable salt thereof; useful in treating arteriosclerosis, ulcer, inflammation, allergy, or the like.

6 Claims, No Drawings

DI-TERT-BUTYL(HYDROXY)PHENYLTHIO SUBSTITUTED HYDROXAMIC ACID DERIVATIVES

BACKGROUND OF THE INVENTION

1. Field of the Invention

This invention relates to the hydroxamic acid derivatives subsituted by di-tert-butyl(hydroxy)phenylthio residue which may be useful as medicine. More particularly, it relates to the hydroxamic acid derivatives subsituted by di-tert-butyl(hydroxy)phenylthio residue, which inhibit LDL (Low Density Lipoprotein) from being incorporated into macrophages, whereby they may be useful as an anti-arteriosclerosis agent.

Besides, they have also anti-oxidation activities to show preventive activity to oxidation of lipid, ulcer formation, and lipoxygenase action, whereby they may be useful as agent for vessel disorder, anti-asthma agent, anti-diabetes agent, anti-ulcer agent, anti-inflammatory agent, anti-tumor agent, anti-allergy agent, and the like.

2. Description of the Prior Art

Atherosclerosis recognized to be a significant symptom which occurs in an initial stage of arteriosclerosis, in such a manner that lipid material mainly consisting cholesterol moves into the arterial wall accompanied by hyperplasia and consequent sclerosis. Atherosclerosis has been thought not to occur due to a single factor but accumulated factors over a long period of time, such as hypertension, hyperlipemia, excessive cigarette smoking, obesity, diabetes mellitus, hyperuricemia, stress, heredity, lack of exercise, etc. Among those factors, the behavior of cholesterol existing as LDL in blood is noted. What is especially important are penetration of LDL into the arterial wall and the incorporation of LDL into macrophages, and the subsequent accumulation of cholesterol at the wall and the vessel disorder. On the other hand, the following factors are considered to promote the occurrence of atherosclerosis: the increase of blood cholesterol due to the troubles on the incorporation of LDL into liver and the metabolism of LDL in liver, the hydrodynamic state of blood due to the change in the physical properties of red blood cell, the damage of endothelium, the abnormal hyperplasia of the arterial wall and the depression of the lipid utilization in arterial tissues, and the like.

For the drug therapy of atherosclerosis, there have heretofore been used anti-arteriosclerosis agents such as pyridinol carbamate; lipid lowering agents such as chlofibrate, nicotinic acid, alpha-tyroxine and chloestyramine; and antiplatelet agents such as dipyridamole and aspirin, etc. The analogues which have activities of lowering lipids in serum or lipoxygenase inhibitory activities are disclosed in U.S. Pat. Nos. 4,029,812, 4,076,841, 4,078,084, EP 273451, or the like. The hydroxamic acid derivatives which have lipoxygenase inhibitory activity are disclosed in JP. Unexam. Publn. No. 86-257951, JP. Unexam. Publn. No. 86-251640, JP. Unexam. Publn. No. 86-251641, JP. Unexam. Publn. No. 86-251642, JP. Unexam. Publn. No. 88-225340, JP. Unexam. Publn. No. 89-104033, JP. Unexam. Publn. No. 89-153658, EP 279263, or the like. This invention characterized by the hydroxamic acid derivatives having di-tert-butyl(hydroxy)phenylthio moiety is new. GB 2,212,153 is quite relavant to the present invention. However, this generally discloses a certain compound of the present invention while it does not specifically disclose such compound.

SUMMARY (Di-tert-Butylhydroxyphenyl)thio subsituted hydroxamic acid derivatives of the formula:

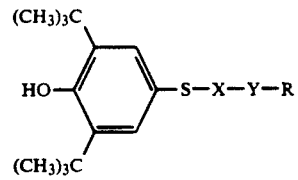

wherein X is straight or branched $C_1$ to $C_{15}$ alkylene which may be attached to Y through phenylene, provided that X is not n-butylmethylene; Y is CO—N(OH) or N(OH)—CO; and R is hydrogen, stright or branched $C_1$ to $C_9$ alkyl, $C_3$ to $C_9$ cycloalkyl, aryl, or aralkyl, provided that R is not hydrogen when Y—R is N(OH)—CO—R; or a pharmaceutically acceptable salt thereof.

Said compounds which inhibit LDL from being incorporated by macrophages and oxidizing fatty acids are useful in treating arteriosclerosis, ulcer, inflammation, or allergy.

DESCRIPTION OF THE PREFERRED EMBODIMENTS

It is generally considered that normal LDL are not incorporated by reticuloendothelial cells (scavenger cells) such as macrophages and kupffer cells, but denaturated LDL are incorporated thereto through a receptor for denaturated LDL. Also, it is considered that even when a large amount of cholesterol is accumulated in cells, the receptor for denaturated LDL does not decrease in number in cells, so that the accumulation of chloesterol is unlimitedly enhanced whereby the conversion of reticuloendothelial cells into foam cells may take place resulting in establishment of arteriosclerosis. It is found that the lipoxygenase in endothelium plays an important role in oxidation and denaturation of LDL [D. Steinberg et al., Proc. Natl. Acad. Sci., 86, 1046, (1989)] and it suggests that the applicability of the compounds having lipoxygenase inhibitory activity as an anti-arteriosclerosis agents.

From the view, as discussed above, that inhibition of the production of denaturated LDL is useful in the prophylaxis or treatment of atherosclerosis, it is desired to develop drugs which can do that.

As a result of extensive studies, the present inventors provided the compounds of the following formula:

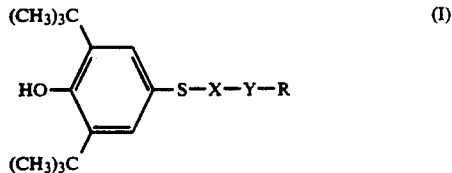

wherein X is straight or branched $C_1$ to $C_{15}$ alkylene which may be attached to Y through phenylene, provided that X is not n-butylmethylene; Y is CO—N(OH) or N(OH)—CO; and R is hydrogen, straight or branched $C_1$ to $C_9$ alkyl, $C_3$ to $C_9$ cycloalkyl, aryl, or aralkyl, provided that R is not hydrogen when Y—R is N(OH)—CO—R; or a pharmaceutically acceptable salt thereof, found that they have excellent anti-oxidative activity such as LDL denaturation inhibitory activity, lipoxygenase inhibitory activity, or the like and completed this invention.

In more detail, this invention provides the compounds of the formula (Ia):

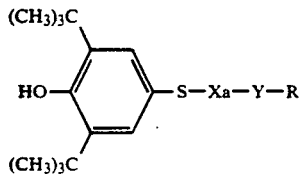

wherein Xa is straight or branched $C_1$ to $C_{15}$ alkylene, provided that Xa is not n-butylmethylene; Y is CO—N(OH) or N(OH)—CO; and R is hydrogen, straight or branched $C_1$ to $C_9$ alkyl, $C_3$ to $C_9$ cycloalkyl, aryl, or aralkyl, provided that R is not hydrogen when Y—R is N(OH)—CO—R; or a pharmacuetically acceptable salt thereof. And the compounds of the formula (Ib):

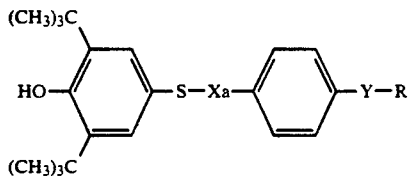

wherein Xa is straight or branched $C_1$ to $C_{15}$ alkylene; Y is CO—N(OH) or N(OH)—CO; and R is hydrogen, straight or branched $C_1$ to $C_9$ alkyl, $C_3$ to $C_9$ cycloalkyl, aryl, or aralkyl, provided that R is not hydrogen when Y—R is N(OH)—CO—R; or a pharmacuetically acceptable salt thereof.

In this specification, the term "straight or branched $C_1$ to $C_{15}$ alkylene" in "X" or "Xa" includes, for example, straight alkylene, e.g., methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, branched alkylene e.g., methylmethylene, dimethylmethylene, propylene, ethylethylene, 1,1-dimethylethylene, n-butylmethylene, 1,1-dimethyltrimethylene, 1,1-dimethyltetramethylene, 1-ethyltetramethylene, 1,1-dimethylpentamethylene, 1-methylhexamethylene, 1,1-dimethylhexamethylene, 1,1-dimethylheptamethylene, 1-methyloctamethylene, 1,1-dimethyloctamethylene, 1,1-dimethylnanomethylene, 1-methyldecamethylene, 1,1-dimethyldecamethylene, 1-methylundecamethylene, 1,1-dimethylundecamethylene, 1,1-dimethyldodecamethylene, 1-methyltridecamethylene, 1,1-dimethyltridecamethylene, 1-methyltetradecamethylene, 1,1-dimethyltetradecamethylene, or 1,1-dimethylpentadecamethylene, and the like. "X" or "Xa" is not simply n-butylmethylene.

Phenylene may intervene between X and Y as shown in the formula (Ib).

The term "straight or branched $C_1$ to $C_9$ alkyl" in "R" includes, for example, methyl, ethyl, propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-noyl, or the like. The term "$C_3$ to $C_9$ cycloalkyl" includes, for example, cyclopropyl, cyclobutyl, cyclopentyl, cyclohexyl, cycloheptyl, cyclooctyl, cyclononyl, and the like. The "aryl" means aromatic moiety which may have one or more subsituents, including, for example, phenyl, cumenyl (o—, m—, p—), mesityl, tolyl (o—, m—, p—), xylyl (2,3—; 2,4—; 2,5—; 3,4—; 3,5—), naphtyl (1—, 2—), indenyl (2—, 3—), or the like. The term "aralkyl" means $C_1$ to $C_4$ alkyl (e.g., methyl, ethyl, propyl, or butyl) which is substituted by one or more aforementioned "aryl" at the any positions, including, for example, benzyl, diphenylmethyl, triphenylmethyl, phenethyl, 3-phenylpropyl, 4-phenylbutyl, naphtylmethyl, indenylmethyl, and the like.

The terms "leaving group" in "Z" means "nucleophilic leaving group" which is ordinarily used including hydroxy, alkoxy, anhydride residue, halogen (e.g., bromine, chlorine, iodine), amine, or the like.

As a preferable "R", it is exemplified that straight or branched $C_1$ to $C_8$ alkyl, for example, methyl, ethyl, propyl, isopropyl, n-butyl, tert-butyl, n-pentyl, n-hexyl, n-heptyl, or n-octyl; $C_3$ to $C_8$ cycloalkyl, for example, cyclopropyl, cyclobutyl, cyclopentyl, cyclohexyl, cycloheptyl, or cyclooctyl; aryl, for example, phenyl, or p-tolyl; aralkyl, for example, benzyl, 4-methylbenzyl, or phenethyl.

The compounds of formula (I) may form a salt with alkali metal (e.g., lithium, sodium, potassium, or the like), with alkaline earth metal (e.g., calcium or the like), with amino acid (e.g., lysine, arginine, or the like), with organic base (e.g., triethylamine, dicyclohexylamine, or the like), or the like.

The compounds of this invention can be prepared according to a conventional method of hydroxamic acid derivatives, for example, as shown in "Organic Functional Group Preparations", Vol. III, Alfred T. Blomquist et al., Academic Press, New York, 1972.

The compounds (I) of this invention can be prepared by the usual methods for preparations of hydroxamic acid such as (1) reaction of a carboxylic acid derivative (e.g., ester, acid halogenide, acid amide, lactam, or the like) with a hydroxylamine or its hydrochloride which have a desirable R moiety under heating, if necessary, in the presence of a base (e.g., alkali alkoxide, alkali hydroxide, sodium hydrogencarbonate, or the like), (2) mild alkali hydrolysis of O,N-diacyl derivative, which is prepared by treatment of an acid anhydride with hydroxylamine, (3) addition of a hydroxylamine with a ketene (4) reaction of a nitro compound in the presence of sulfuric acid under mild condition, or (5) oxidization of a nitrogen containing compound (e.g., oxime, amine, imine, or the like) with a peroxide (e.g., peroxodisulfuric acid, hydrogen peroxide, or the like).

For example, the compound can be preferably prepared, as follows.

(A) When Y—R is —CO—N(OH)R.

Route 1

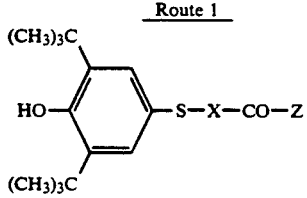

Step 1

-continued
Route 1

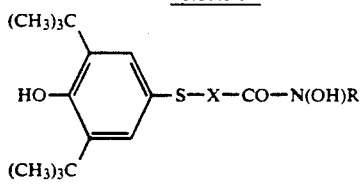
(IA)

In the reaction scheme, X and R each has the same meaning as defined before and Z is nucleophilic leaving group.

Step 1

In this step, a carboxylic acid derivative (II) is converted into the compound of this invention (IA).

In the reaction of the compound (II) wherein Z is hydroxy, with carboxylic acid activator, the activator such as thionyl chloride, phosphours oxychloride, phosphorus pentachloride, chlorocarbonates (e.g., methyl chlorocarbonate, ethyl chlorocarbonate, isobutyl chlorocarbonate), oxalyl chloride, carbodiimides (e.g., N,N-dicyclohexylcarbodiimide (DCC)) or the like is used. Carbodiimides may be used together with p-nitrophenol or hydroxysuccinimide.

The reaction is carried out in a solvent such as halogenated hydrocarbon (e.g., dichloromethane, chloroform), ether (e.g., diethyl ether, isopropyl ether, tetrahydrofuran, dioxane), N,N-dimethylformaide, or acetonitrile or their mixed solvent. The reaction temperature is usually −50° C. to 50° C.

In this reaction when thionyl chloride, phosphorus oxychloride, oxalyl chlroide, or phosphorus pentachloride is used as a carboxylic acid activator, an acid halide is prepared as a reactive derivative, when a chlorocarbonate is used, a mixed acid anhydride is prepared, and when carbodiimide is used, active ester is prepared.

The reaction of the compound (II) with hydroxylamine is carried out as follows: when the compound (II) is an acid halide, the reaction is carried out in a solvent such as dichloromethane, tetrahydrofuran, acetone, or the like in the presence of a base (e.g., pyridine, 4-dimethylaminopyridine, triethylamine, sodium hydroxide, potassium hydroxide, potassium carbonate, sodium carbonate, potassium hydrogencarbonate, sodium hydrogencarbonate, or the like) under the dry or water containing condition. The reaction temperature is about −30° C. to about 50° C.; when the compound (II) is active ester or mixed acid anhydride, the reaction is carried out in the same solvent which is used in the reaction of the compound (II) wherein R is hydroxy, with a carboxylic acid activator. The reaction temperature is usually −20° C. to 50° C. and the reaction time is 1 to 5 hours.

The compound (II) wherein Z is hydroxy may be directly converted into hydroxamic acid in the presence of a condensing agent.

Route 2

$R_1-X-CO-Z$ (IV)

↓ Step 1

Hal-X—CO—N(OH)R (VA)

↓ Step 2

-continued
Route 2

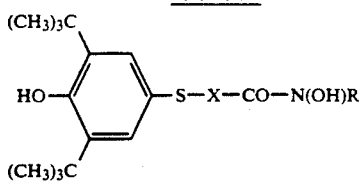
(IA)

In the reaction scheme, $R_1$ is hydroxy or halogen; Hal is halogen; X, Z, and R each is the same as defined before.

Step 1

In this step, a carboxylic acid derivative (IV) is converted into the hydroxamic acid (VA) having desirable "R" moiety through an acid halide.

The halogenation and the hydroxamic acid formation in this step can be carried out according to the same procedure as shown in Step 1 of Route 1. When $R_1$ is hydroxy, it is also halogenated at the same time in this step.

Step 2

In this step, the compound (VA) is allowed to react with 2,6-di-tert-butyl-4-mercaptophenol to give the compound (IA) of this invention.

The reaction is carried out in the presence of a base (e.g., sodium hydroxide, potassium hydroxide, carcium hydroxide, potassium carbonate, pyridine, 4-dimethylaminopyridine, triethylamine, or the like) in a solvent such as an alcohol (e.g., methanol, ethanol, propanol, tert-butanol, or the like), an ether (e.g., diethyl ether, tetrahydrofuran, or the like), N,N-dimethylacetoamide, or acetonitrile under cooling, at room temperature, or under refluxing for 10 minutes to several ten hours. When the reaction is carried out under the condition like using a immiscible base with a solvent system, for example, using a base such as alkali hydroxide or alkali carbonate in a solvent such as an alcohol (e.g., methanol, ethanol, propanol, tert-butanol, or the like), halogenated hydrocarbon (e.g., dichloromethane, chloromethane, dichloroethane, or the like) or an aromatic hydrocarbon (e.g., benzene, toluene, or the like), the reaction may be carried out in the presence of the phase transfer catalyst such as tetra-n-butylammonium iodide in the single layer of the said solvent or two layers with water.

(B) When Y—R is —N(OH)CO—R.

Route 3

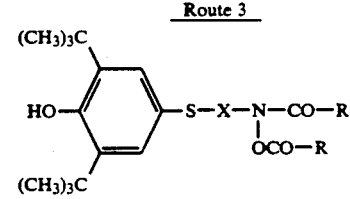
(VI)

↓ Step 1

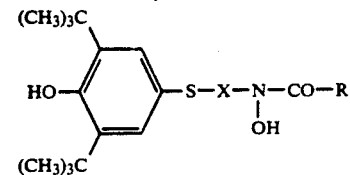
(IB)

In the reaction scheme, X and R, each has the same meaning as defined before.

Step 1

In this step, an O,N-diacyl derivative (VI) is converted into the compound (IB) of the present invention.

This step is carried out by mild hydrolysis of the O,N-diacyl derivative (VI) with alkali hydroxide (e.g., lithium hydroxide, sodium hydroxide, potassium hydroxide, barium hydroxide, or the like) by a usual manner.

The said O,N-diacyl derivative (VI) may be prepared as shown below.

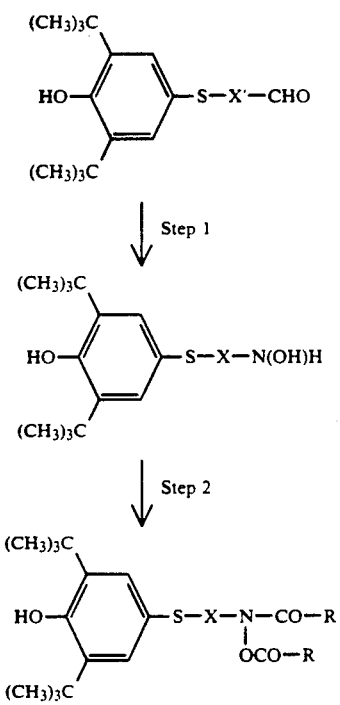

In the reaction scheme, X' is alkylene which remove one methylene from Xa; and X, Xa, and R, each is the same as defined before.

Step 1

In this step, an aldehyde (VII) is converted into an oxime which is further reduced to give a compound (VII').

The oxime formation is carried out by reacting a compound (VII) with hydroxylamine according to a ususal manner.

The reduction of a hydroxyimino moiety in the resulting compound into a hydroxylamino moiety is carried out in a usual manner using a borane reagent such as borane tetrahydrofuran, borane amine (e.g., borane pyridine, borane trimethylamine, borane triethylamine, borane morpholine, or the like), borane sulfate (e.g., borane dimethylsulfate, or the like), or borane phosphine (e.g., borane tri-n-butylphosphine, borane triphenylphosphine, or the like), hydroxide (e.g., sodium borohydride, trimethoxyaluminiumlithium hydride, tri-tert-butyoxyaluminiumlithium hydride, or the like), acid-zinc (e.g., acetic acid-zinc, hydrochloric acid-zinc, or the like), or sodium metalmethoxyethoxymethane in a solvent such as ether (e.g., diethyl ether, tetrahydrofuran, or the like), alcohol (e.g., methanol, ethanol, or the like), or their mixture.

The compound (VII') which have phenylene between "Xa" and nitrogen can be prepared, for example, by reduction of a nitrocompound of the formula:

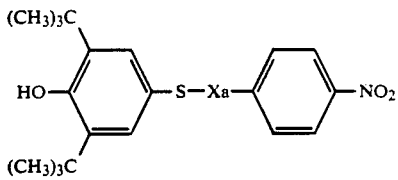

wherein Xa has the same meaning as defined before, or its nitroso-compound.

Step 2

In this step, the hydroxylamine (VII') is acylated to give the compound (VI) of the present invention.

This step is carried out by acylation of the compound (VII') into an O,N-diacyl derivative with an acylating agent such as an acid anhydride or acid halide which has a desired R moiety, in the presence of a base (e.g., pyridine, 4-dimethylaminopyridine, triethylamine, or the like).

As an alternative method, the compounds (IB) of this invention may be prepared by S-alkylation of 2,6-tert-butyl-4-mercaptophenol with the compound of the formula:

Hal—X—N(OH)—CO—R wherein Hal, X, and R, each has the same meaning as defined before.

The compounds (I) of this invention thus prepared can be isolated by conventional separation and purification method (e.g., chromatography, crystallization, or the like).

EFFECT OF THE INVENTION

The compounds (I) of this invention can strongly inhibit the incorporation of LDL into macrophages, the oxidation of lipid, the formation of ulcer, and/or action of lipoxygenase. Therefore, they are useful for prevention and treatment of arteriosclerosis, gastric ulcer, allergic diseases, rheumatoid athritis, myocardial ischemia, cataract, liver injury, cerebral cell disturbance, diabetes mellitus, thyrioid function disorder, malignant tumor, inflammatory disease, or the like.

The compounds (I) of this invention can be administered orally or parenterally to patients. For the oral administration, they are normally formulated into conventional preparation form such as solid preparations (e.g., tablets, powders, capsules, granyles) or liquid preparations (e.g., aqueous dispersion, oily suspension, syrups, elixirs). For the parenteral administration, they are usually applied injectionablly, such as in aqueous solutions or oily dispersions. On the formulation of the above preparations, excipients, binding agent, lubricants, solvents, solubilizers, emulsifiers, dispersants, and the like may be used. Other additives such as preservatives and stabilizing agents may be also used.

The dosage of the compounds (I) of this invention varies with the dosage form, age, bodyweight, symptom of the patient, or the like but usually ranges from about 5 to 1000 mg per day, preferably, 20 mg to 200 mg per day for oral administration and 1 mg to 500 mg per day, preferably, 5 mg to 50 mg per day for parenteral administration. These may be administered in single or divided doses.

Practical and presently preferred embodiments for this invention are shown in the following Examples, but it should be understood that these examples are given only for the illustrative purposes and do not limit the scope of the present invention thereto.

EXAMPLE 1

N-Methyl-2-(3,5-di-tert-butyl-4-hydroxyphenyl)thioacetohydroxamic acid (I1)

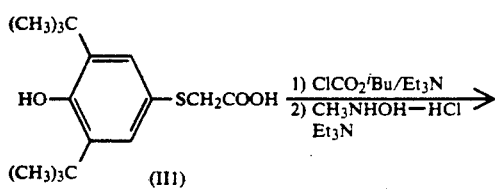

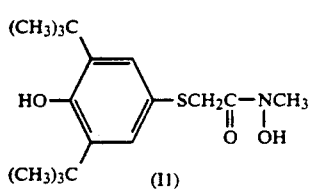

To 20 ml of a solution of 1.48 g (5 mmol) of 2-(3,5-di-tert-butyl-4-hydroxyphenyl)thioacetic acid (III) in dichloromethane was added 555 mg (5.5 mmol) of triethylamine and 5 ml of a solution of 750 mg (5.5 mmol) of isobutyl chlorocarbonate in dichloromethane was added dropwise to the resulting mixture over an about 5 minutes period under cooling at $-45°$ C.$\pm 5°$ C. and stirring. The mixture was stirred for 1 hour at the same temperature. To the reaction mixture was added 450 mg (5.5 mmol) of N-methyl hydroxylamine hydrochloride and then added dropwise 5 ml of a solution of 1.21 g (12 mmol) of triethylamine in dichloromethane. The mixture was stirred at the same temperature for 30 minutes and then additional 2 hours after removal of the cooling bath. The reaction mixture was poured into 50 ml of a cold 5% aqueous solution of hydrochloric acid and extracted with 50 ml of dichloromethane. The extract was washed twice with 50 ml of water, dried over anhydrous sodium sulfate and concentrated under reduced pressure. The residue was chromatographed on silica gel. The fractions eluted with a mixture of ethyl acetate-n-hexane (2:1) were collected. From the first fraction, 892 mg of isobutyl 2-(3,5-di-tert-butyl-4-hydroxyphenyl)thioacetate was obtained as colorless oil in 55% yield and the aimed compound (I1) obtained from the second fraction was recrystallized from a mixture of ether-n-hexane (1:1) to give 350 mg of colorless prismatic crystals in 21.5% yield. Mp. 84°-85° C.

Analysis Calcd. (%) for $C_{17}H_{27}NO_3S$: C, 62.74; H, 8.36; N, 4.30; S, 9.85; Found: C, 62.67; H, 8.31; N, 4.39; S, 9.82. IR $\nu$max(Nujol)cm$^{-1}$: 3580, 3180(OH), 1625 (CO). 200 MHz NMR(CDCl$_3$)$\delta$: 1.43(18H, s, 2$\times$C(CH$_3$)$_3$), 3.06(3H, s, NCH$_3$), 3.55(2H, broad, —SCH$_2$—), 5.34(1H, broad, —OH), 7.33(2H, s, 2$\times$aromatic H).

EXAMPLE 2

N-Methyl-3-(3,5-di-tert-butyl-4-hydroxyphenyl)thiopropohydroxamic acid (I2)

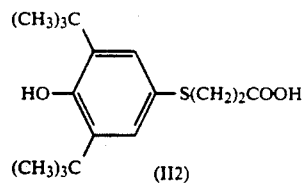

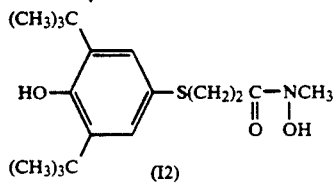

To 30 ml of a solution of 2.17 g (7 mmol) of 3-(3,5-di-tert-butyl-4-hydroxyphenyl)thiopropionic acid (II2) in dichloromethane was added 717 mg (7.1 mmol) of triethylamine and to the mixture was added 870 mg (8 mmol) of ethyl chlorocarbonate under stirring and ice-cooling. The resulting mixture was stirred for 30 minutes under ice-cooling, then 1.25 g (15 mmol) of methylhydroxylamine hydrochloride and 3.03 g (30 mmol) of triethylamine were added thereto, and the mixture was stirred at room temperature for 2 hours. The reaction mixture was poured into 50 ml of a 5% aqueous solution of hydrochloric acid and extracted with 50 ml of dichloromethane. The extract was washed with 50 ml of water twice, dried over anhydrous sodium sulfate, and concentrated under reduced pressure. The residue was chromatographed on silica gel and the fraction eluted with a mixture of ethyl acetate-ether (3:1) were collected to give crystalline residue which was recrystallized from a mixture of ether-n-hexane (1:1) to give 1.166 g of the aimed compound as colorless prismatic crystals in 49.1% yield. Mp. 103°-105° C.

Anal. Calcd. (%) for $C_{18}H_{29}NO_3S$: C, 63.68; H, 8.61; N, 4.13; S, 9.44; Found: C, 63.32; H, 8.59; N, 4.08; S, 9.24. IR $\nu$max(Nujol)cm$^{-1}$: 3605, 3590, 3180(OH), 1616(CO). 200 MHz NMR(CDCl$_3$)$\delta$: 1.37(18H, s, 2$\times$C(CH$_3$)$_3$), 2.54(2H, broad, —CH$_2$CO—), 307(2H, t, J=7.5 Hz, —SCH$_2$—), 3.22(3H, s, NCH$_3$), 5.21(1H, broad, OH), 7.21(2H, s, 2$\times$aromatic H).

EXAMPLES 3 to 7

According to the procedure shown in Example 2, the following compounds and the compounds shown in Table 2 were prepared under the reaction conditions shown in Table 1.

EXAMPLE 3

Preparation of N-methyl-4-(3,5-di-tert-butyl-4-hydroxyphenyl)thiobutyrohydroxamic acid (I3)

EXAMPLE 4

Preparation of N-methyl-5-(3,5-di-tert-butyl-4-hydroxyphenyl)thiovalerohydroxamic acid (I4)

EXAMPLE 5

Preparation of 5-(3,5-di-tert-butyl-4-hydroxyphenyl)-thiovalerohydroxamic acid (I5)

EXAMPLE 6

Preparation of N-methyl-6-(3,5-di-tert-butyl-4-hydroxyphenyl)thiocaprohydroxamic acid (I6)

EXAMPLE 7

Preparation of N-methyl-4-(3,5-di-tert-butyl-4-hydroxyphenyl)thiomethylbenzohydroxamic acid (I7)

TABLE 1

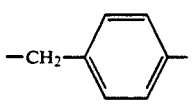

| Ex. No. | —X— | —R | II mg(mmol) | NEt₃ mg(mmol) | ClCO₂Et mg(mmol) | R—NHOH.HCl mg(mmol) | NEt₃ mg(mmol) |
|---|---|---|---|---|---|---|---|
| 3 | —(CH₂)₃— | —CH₃ | 1620 (5) | 555 (5.5) | 650 (6) | 540 (6.5) | 1520 (15) |
| 4 | —(CH₂)₄— | —CH₃ | 1690 (5) | 555 (5.5) | 650 (6) | 540 (6.5) | 1520 (15) |
| 5 | —(CH₂)₄— | —H | 340 (1) | 121 (1.2) | 120 (1.1) | 105 (1.5) | 303 (15) |
| 6 | —(CH₂)₅— | —CH₃ | 2390 (6.78) | 707 (7) | 760 (7) | 835 (10) | 2020 (20) |
| 7 | —CH₂—C₆H₄— | —CH₃ | 2980 (8) | 909 (9) | 977 (9) | 835 (10) | 2020 (20) |

| Ex. No. | Purification | Yield mg (%) |
|---|---|---|
| 3 | Recrystallization (ether) | 985 (55.8) |
| 4 | Recrystallization (ether-methanol) | 1530 (83.3) |
| 5 | 1) Column chromatography on silica gel (ethyl acetate) 2) Recrystallization (ether-n-hexane (1:1)) | 210 (59.4) |
| 6 | Recrystallization (ether-methanol) | 2080 (80.4) |
| 7 | 1) Column chromatography on silica gel (ether-ethyl acetate (1:1)) 2) Recrystallization (ether-n-hexane (1:1)) | 1210 (37.7) |

TABLE 2

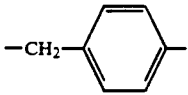

| Ex. No. | —X— | —R | Appearance | Mp. (°C.) | IRνmax Nujol (cm⁻¹) |
|---|---|---|---|---|---|
| 3 | —(CH₂)₃— | —CH₃ | Colorless prismatic crystal | 112~113 | 3600, 3580, 3185(OH), 1595(CO). |
| 4 | —(CH₂)₄— | —CH₃ | Colorless needle-like crystal | 121~122 | 3595, 3100(OH), 1615sh(CO). |
| 5 | —(CH₂)₄— | —H | Colorless needle-like crystal | 121~123 | 3600, 3280sh, 3200(OH), 1638(CO). |
| 6 | —(CH₂)₅— | —CH₃ | Colorless needle-like crystal | 109~111 | 3600, 3120, 3040sh(OH), 1586(CO). |
| 7 | —CH₂—C₆H₄— | —CH₃ | Colorless prismatic crystal | 119~120 | 3600, 3220(OH), 1637(CO). |

| Ex. No. | 200 MHz NMR δ ppm(CDCl₃) | Analysis (Molecular Formula) Calcd. (%): Found (%): |
|---|---|---|
| 3 | 1.37(18H, s, 2×C(CH₃)₃), 1.92(2H, quint, —CH₂C$\underline{H}$₂CH₂—), 2.46(2H, broad, —CH₂CO—), 2.85(2H, t, J=7Hz, —SCH₂—), 5.22(1H, broad, OH), 7.18(2H, s, 2×aromatic H). | (C₁₉H₃₁NO₃S) C. 64.55; H, 8.84; N, 3.96; S, 9.07 C, 64.31; H, 8.83; N, 3.94; S, 8.99 |
| 4 | 1.43(18H, s, 2×C(CH₃)₃), 1.63-1.90(4H, m, —CH₂CH₂—), 2.39(2H, broad, CH₂CO—), 2.85(2H, t, J=7Hz, —SCH₂—), 3.33(3H, s, NCH₃), 5.22(1H, broad, OH), 7.23(2H, s, 2× aromatic H). | (C₂₀H₃₃NO₃S) C, 65.36; H, 9.05; N, 3.81; S, 8.72 C, 64.98; H, 9.04; N, 3.76; S, 8.64 |
| 5 | 1.43(18H, s, 2×C(CH₃)₃), 1.61-1.88(4H, m, —CH₂CH₂—), 2.19(2H, t, J=7.5Hz, —CH₂CO—), 2.83(2H, t, J=7Hz, —SCH₂—), 5.22(2H, broad, OH), 7.22(2H, s, 2×aromatic H). | (C₁₉H₃₁NO₃S) C, 64.55; H, 8.84; N, 3.96; S, 9.07 C, 64.27; H, 8.83; N, 4.29; S, 9.36 |

TABLE 2-continued

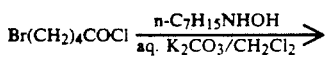

| 6 | 1.43(18H, s, 2×C(CH₃)₃), 1.44–1.78(6H, m, 3×CH₂), 2.35 (2H, broad, —CH₂CO—), 2.83(2H, t, J=7Hz, —SCH₂—), 3.33 (3H, s, NCH₃), 5.20(1H, broad, OH), 7.22(2H, s, 2× aromatic H). | ($C_{21}H_{35}NO_3S$) C, 66.10; H, 9.25; N, 3.67; S, 8.40 C, 65.85; H, 9.18; N, 3.62; S, 8.30 |
|---|---|---|
| 7 | 1.37(18H, s, 2×C(CH₃)₃), 3.41(3H, s, NCH₃), 3.98(2H, s, —SCH₂), 5.28(1H, broad, OH), 7.10(2H, s, 2×aromatic H), 7.25, 7.45(each 2H, AB, $J_{AB}$=7.5Hz, 4×aromatic H). | ($C_{23}H_{31}NO_3S$) C, 68.79; H, 7.78; N, 3.49; S, 7.98 C, 68.74; H, 7.71; N, 3.35; S, 7.88 |

EXAMPLE 8

N-n-Heptyl-5-(3,5-di-tert-butyl-4-hydroxyphenyl)thiovalerohydroxamic acid (I8)

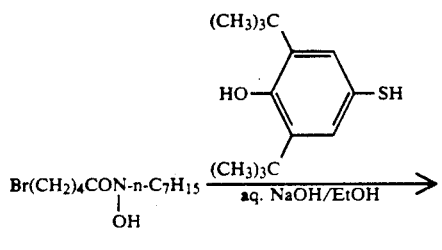

A mixture of 1.5 g (8.3 mmol) of 5-bromovaleric acid and 1 ml of thionyl chloride was heated for 1 hour at 50° C. and the remainder thionyl chloride was evaporated under reduced pressure to give the crude 5-bromovaleryl chloride (IV1'). To a mixture of 50 ml of a solution of 1.31 g (10 mmol) of n-heptylhydroxylamine in dichloromethane and 20 ml of an aqueous solution of 1.38 g (10 mmol) of potassium carbonate was added dropwise 50 ml of a solution of the compound (IV1') in dichloromethane under stirring and ice-cooling. After addition, the mixture was stirred for 2 hours at room temperature. To the reaction mixture was poured 50 ml of a 5% aqueous solution of hydrochloric acid. The separated dichloromethane layer was washed with 50 ml of water twice, dried over anhydrous sodium sulfate, concentrated under reduced pressure to give the crude product (V1) as a pale yellow oil. The oil was chromatographed on silica gel and from the fractions eluted with a mixture of ether-n-hexane (1:1), 1.66 g of the pure product (V1) was prepared in 68% yield as colorless oil. To 5 ml of a solution of 560 mg (1.9 mmol) of the compound (V1) in ethanol are added 477 mg (2 mmol) of 2,6-di-tert-butyl-4-mercaptophenol and 1 ml of an aqueous solution of 200 mg of sodium hydroxide and the mixture was stirred for four hours at room temperature. To the reaction mixture which was cooled in an ice bath was added 20 ml of a 5% aqueous solution of hydrochloric acid and the resulting mixture was extracted with 50 ml of ether. The ether layer was washed 50 ml of water twice, dried over anhydrous sodium sulfate, concentrated under reduced pressure. The oily residue was chromatographed on silica gel and 370 mg of the aimed compound (I8) was obtained in 43% yield as a pale yellow oil from the fraction eluted with ether.

Anal. Calcd. (%) for $C_{26}H_{45}NO_3S$: C, 69.13; H, 10.04; N, 3.10; S, 7.10; Found (%): C, 68.84; H, 9.93; N, 3.11; S, 6.97. IR $\nu$max(film)cm$^{-1}$: 3640, 3180(OH), 1615(CO). 200 MHz NMR δ ppm(CDCl₃): 0.83(3H, t, J=7 Hz, —CH₂CH₃), 1.24 (10H, s, 5×CH₂), 1.38(18H, s, 2×C(CH₃)₂), 1.57–1.82(4H, m, 2×CH₂), 2.28 (2H, broad, —CH₂CO—), 2.80(2H, t, J=7 Hz, —SCH₂—), 3.55(2H, t, J=7 Hz, —NCH₂—), 5.20(1H, broad, OH), 7.17(2H, s, 2×aromatic H).

EXAMPLE 9

N-Cyclohexyl-5-(3,5-di-tert-butyl-4-hydroxyphenyl)-thiovalerohydroxamic acid (I9)

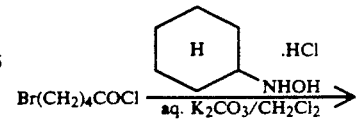

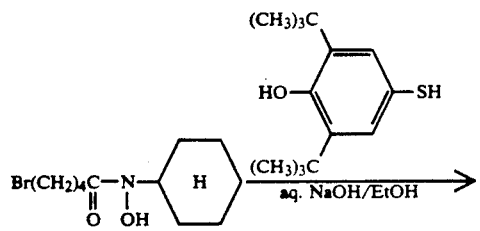

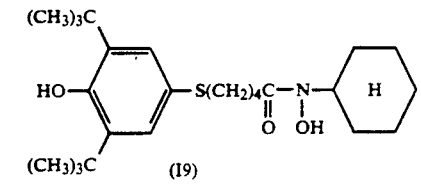

The compound (IV1') which was prepared from 1.81 g (10 mmol) of 5-bromovaleric acid (IV1) and 1 ml of thionyl chloride according to the procedure shown in Example 8 was allowed to react with 1.75 g (11.5 mmol) of N-cyclohexylhydroxylamine hydrochloride to give the crude N-cyclohexyl-5-bromovalerohydroxamic acid (V2) as a pale yellow oil. Without further purification the oil was added to 20 ml of a solution of 2.83 g (10 mmol) of 2,6-di-tert-butyl-4-mercaptophenol in ethanol and then 10 ml of an aqueous solution of 1 g (25 mmol) of sodium hydroxide was added thereto and the mixture was stirred for 4 hours at room temperature. To the reaction mixture was added 50 ml of a 5% aqueous solution of hydrochloric acid under ice-cooling and the mixture was extracted with 100 ml of dichloromethane. The organic layer was washed with 100 ml of water twice, dried over anhydrous sodium sulfate, and concentrated under reduced pressure to give a crystalline residue, which was recrystallized from ether containing small amount of methanol to give 1.82 g of the aimed compound (I9) as colorless prismatic crystals in 49.6%. The physical data are shown in Table 3.

EXAMPLE 10

N-Methyl-7-(3,5-di-tert-butyl-4-hydroxyphenyl)thioheptanohydroxamic acid (I10)

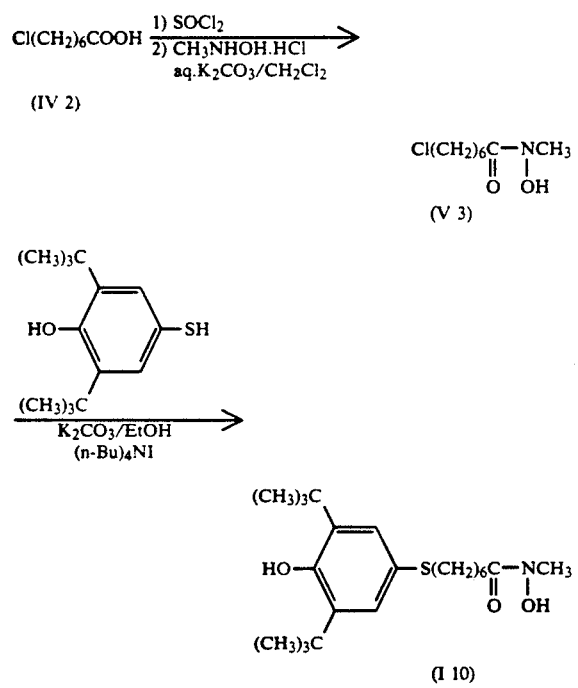

A mixture of 1.64 g (10 mmol) of 7-chloroheptanoic acid and 1 ml of thionyl chloride was heated for 2 hour at 40° C. to 50° C. and the remainder thionyl chloride was evaporated under reduced pressure. A solution of the residue in 10 ml of dichloromethane was added dropwise to 10 ml of an aqueous solution of 1.66 g (12 mmol) of potassium carbonate containing 835 mg (10 mmol) of N-methyl hydroxylamine under stirring and ice-cooling. After addition, the mixture was stirred for 2 hours at room temperature. The reaction mixture was cooled under ice-cooling and 20 ml of a 5% aqueous solution of hydrochloric acid was poured thereto. The mixture was extracted with 50 ml of dichloromethane and the dichloromethane layer was washed with 50 ml of water twice, dried over anhydrous sodium sulfate, concentrated under reduced pressure to give the crude N-methyl-7-chloroheptanohydroxamic acid (V3) as a pale yellow oil. The oil was subjected to the following reaction without further reaction. To a solution of 1.94 g (10 mmol) of compound (V3) and 2.83 g (10 mmol) of 2,6-di-tert-butyl-4-mercaptophenol in 50 ml of ethanol were added 1.52 g (11 mmol) of potassium carbonate and 50 mg of N-tetra-n-butylammonium iodide. The mixture was refluxed for 4 hours under heating and ethanol was evaporated. To the resulting residue was added 50 ml of a 5% aqueous solution of hydrochloric acid and the mixture was extracted with 50 ml of dichloromethane. The dichloromethane layer was washed with 50 ml of water twice, dried over anhydrous sodium sulfate, concentrated under reduced pressure to give an oily residue. The oil was chromatographed on silica gel to give 2.89 g of the aimed compound (I10) in 73% yield as a colorless to pale yellow oil from the fraction eluted with ether.

EXAMPLE 11

N-Methyl-8-(3,5-di-tert-butyl-4-hydroxyphenyl)thiooctanohydroxamic acid (I11)

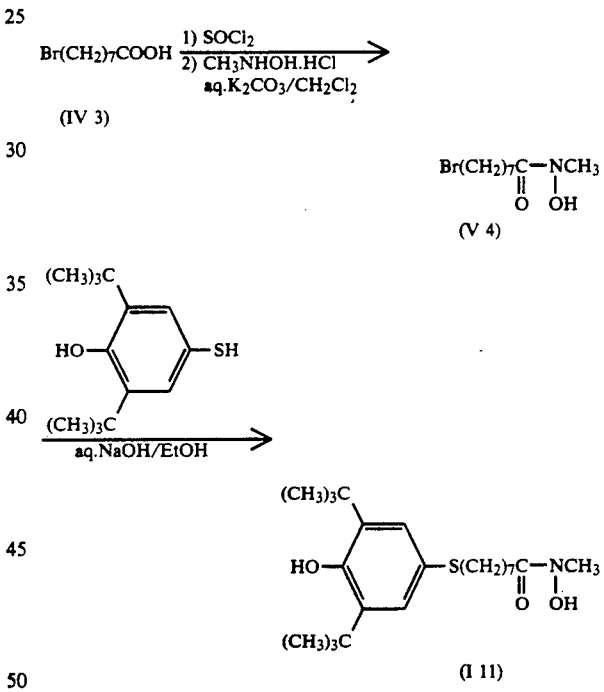

A mixture of 2.23 g (10 mmol) of 8-bromooctanoic acid (IV3) and 1 ml of thionyl chloride was heated for 1 hour at 50° C. and the remainder thionyl chloride was evaporated under reduced pressure. The resulting product was treated with 835 mg (10 mmol) of N-methyl hydroxylamine hydrochloride and 1.66 g (12 mmol) of potassium carbonate according to the procedure shown in Example 10 to give methyl-8-bromooctanohydroxamic acid (V4), which was recrystallized from a mixture of ether-n-hexane (1:1) to give 2.12 g of the compound (V4) as colorless prismatic crystals. mp. 39° C. to 40° C. To a solution of 2.12 g (8.4 mmol) of the compound (V4) and 2.15 g (9 mmol) of 2,6-di-tert-butyl-4-mercaptophenol in ethanol was added of 1.05 g (26.3 mmol) of sodium hydroxide and the resulting mixture was stirred for 4 hours at room temperature. The reaction mixture was poured into 50 ml of a 5% aqueous solution of hydrochloric acid and the mixture was extracted with 100 ml of ether. The ether layer was washed with 100 ml of water twice, dried over anhydrous sodium sulfte, and concentrated under reduced pressure to give an oily residue which was chromatographed on silica gel. The aimed compound (I11) which was obtained from the fraction eluted with a mixture of ether-ethyl acetate (2:1) was recrystallized from n-hexane containing small amount of ether to give 2.99 g of colorless needle-like crystals in 87% yield.

The physical data are shown in Table 3.

EXAMPLE 12

N-Methyl-9-(3,5-di-tert-butyl-4-hydroxyphenyl)thiononanohydroxamic acid (I12)

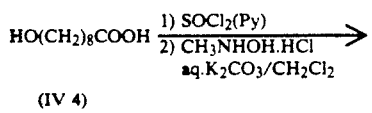

(IV 4)

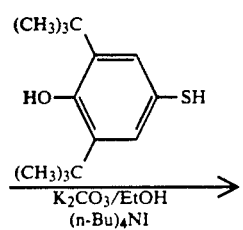

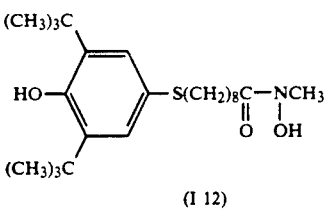

(I 12)

A mixture of 1.02 g (5.85 mmol) of 9-hydroxynonanoic acid (IV4), 1 ml of thionyl chloride, and a drop portion of pyridine was heated for 3 hours on a warm bath at 70° C. and the remainder thionyl chloride was evaporated under reduced pressure. A solution of the resulting residue in 20 ml of dichloromethane was treated with 20 ml of an aqueous solution of 530 mg (6.35 mmol) of methylhydroxylamine hydrochloride and 900 mg (6.5 mmol) of potassium carbonate according to the procedure shown in Example 10 to give N-methyl-9-chlorononanohydroxamic acid (V8), which was chromatographed on silica gel eluted with ether to give 534 mg of the pure compound (V8) as a pale yellow oil in 41.1% yield. A solution of 534 g (2.4 mmol) of the compound (V8) and 580 mg (2.4 mmol) of 2,6-di-tert-butyl-4-mercaptophenol in 10 ml of ethanol was treated in the presence of 414 mg (3 mmol) of potassium carbonate and 20 mg of N-tetra-n-butylammonium iodide according to the procedure shown in Example 9. The product was chromatographed on silica gel and eluted with a mixture of dichloromethane-ethyl acetate (1:1) to give 260 mg of the aimed compound (I12) as a pale yellow oil in 25.5% yield.

The physical data are shown in Table 3.

EXAMPLE 13

N-Methyl-11-(3,5-di-tert-butyl-4-hydroxyphenyl)thioundecanohydroxamic acid (I13)

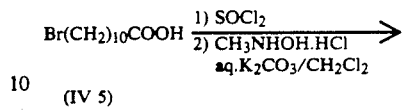

(IV 5)

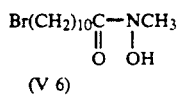

(V 6)

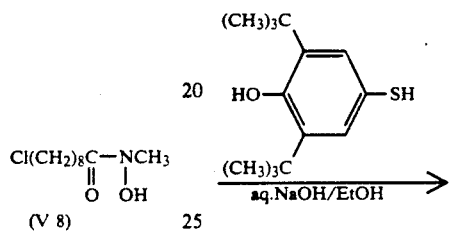

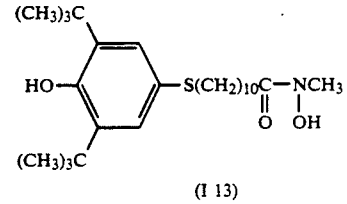

(I 13)

According to the procedure shown in Example 11, 2.65 g (10 mmol) of 11-bromoundecanoic acid (IV5) was treated with 1 ml of thionyl chloride and the resulting product was treated with 850 mg (10.2 mmol) of methylhydroxylamine hydrochloride and 1.5 g (10.9 mmol) of potassium carbonate to give N-methyl-11-bromoundecanohydroxamic acid (V6), which was recrystallized from a mixture of ether-n-hexane to give 2.46 g of the compound (V6) as colorless prismatic crystals in 83.6% yield. mp. 49° C. to 51° C. To a solution of 2.11 g (7.2 mmol) of the compound (V6) was allowed to react with 1.71 g (7.2 mmol) of 3,5-di-tert-butyl-4-hydroxythiophenol under the condition shown in Example 11. The prepared product was chromatographed and eluted with a mixture of ether-ethyl acetate (2:1) to give 3.12 g of the aimed compound (I13) as a pale yellow in 96.3% yield.

The physical data are shown in Table 3.

EXAMPLE 14

N-Methyl-12-(3,5-di-tert-butyl-4-hydroxyphenyl)thiododecahydroxamic acid (I14)

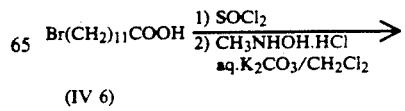

(IV 6)

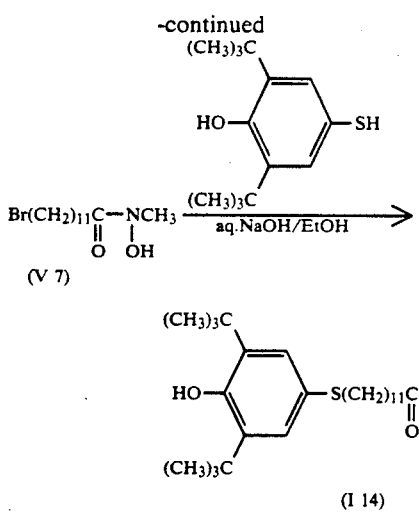

According to the procedure shown in Example 11, 1.4 g (5 mmol) of 12-bromododecanoic acid (IV6) was treated with 1 ml of thionyl chloride and the resulting product was treated with 500 mg (6 mmol) of methylhydroxylamine hydrochloride and 900 mg (6.5 mmol) of potassium carbonate to give N-methyl-12-bromododecahydroxamic acid (V7), which was recrystallized from a mixture of ether-n-hexane (1:1) to give 1.16 g of the compound (V7) as colorless leaflet-like crystals in 75.3% yield. mp. 53° C. to 55° C. To a solution of 1.16 g (3.76 mmol) of the compound (V7) and 900 mg (3.76 mmol) of 2,6-di-tert-butyl-4-mercaptophenol were treated with a mixture of 10 ml of an aqueous solution of 420 mg (10.5 mmol) of sodium hydroxide and 20 ml of ethanol according to the Example 11. The prepared product was chromatographed and the product obtained from the fraction eluted with a mixture of ether-ethyl acetate (2:1) was recrystallized from n-hexane containing small amount of ether to give 1.124 g of the aimed compound (I14) as colorless needle-like crystals in 64.2% yield.

The physical data are shown in Table 3.

TABLE 3

$$\text{HO}-\underset{(CH_3)_3C}{\overset{(CH_3)_3C}{\bigcirc}}-S-X-\underset{\underset{O}{\|}}{C}-\underset{\underset{OH}{|}}{N}R$$

| Ex. No. | X | R | Mp. (°C.) | IR νmax (cm$^{-1}$) |
|---|---|---|---|---|
| 9 | (CH$_2$)$_4$ | Cyclohexyl | 146~148 | Nujol 3580, 3140(OH), 1604, 1585, 1570(CO). |
| 10 | (CH$_2$)$_6$ | CH$_3$ | | film 3615, 3150(OH), 1600(CO). |
| 11 | (CH$_2$)$_7$ | CH$_3$ | 72~73 | Nujol 3635, 3145, 3060(OH). 1627sh, 1605(CO). |
| 12 | (CH$_2$)$_8$ n | CH$_3$ | | film 3640, 3180(OH), 1615(CO). |
| 13 | (CH$_2$)$_{10}$ | CH$_3$ | | film 3640, 3185(OH), 1615(CO). |
| 14 | (CH$_2$)$_{11}$ | CH$_3$ | 76~77 | Nujol 3640, 3160, 3060(OH). 1630, 1605(CO). |

| Ex. No. | 200 MHz NMR δ ppm(CDCl$_3$) | Anaylsis (molecular Formula) Calcd. (%): Found (%): |
|---|---|---|
| 9 | 1.43(18H, s, 2×C(CH$_3$)$_3$), 1.60-1.89(14H, m, 7×CH$_2$), 2.32-2.42(2H, broad, —CH$_2$CO—), 2.86(2H, t, J=7Hz, —SCH$_2$—), 3.60-3.80(1H, broad, N—CH), 5.19(1H, broad, OH), 7.22(2H, s, 2×aromatic H). | (C$_{25}$H$_{41}$NO$_3$S) C, 68.92: H, 9.49; N, 3.22; S, 7.36 C, 68.81; H, 9.60; N, 3.11; S, 7.20 |
| 10 | 1.34-1.74(8H, m, 4×CH$_2$), 1.44(18H, m, 2×C(CH$_3$)$_3$), 2.31-2.33(2H, broad, —COCH$_2$—), 2.83(2H, t, J=7Hz, —SCH$_2$—), 3.33(3H, s, NCH$_3$), 5.19(1H, broad, OH), 7.22(2H, s, 2× aromatic H). | (C$_{22}$H$_{37}$NO$_3$S) C, 66.78; H, 9.43; N, 3.54; S, 8.10 C, 66.53; H, 9.32; N, 3.46; S, 7.92 |
| 11 | 1.29-1.40(6H, m, 3×CH$_2$), 1.43(18H, s, 2×C(CH$_3$)$_3$), 1.56-1.75(4H, m, 2×CH$_2$), 2.27-2.43(2H, broad, —CH$_2$CO—), 2.82 (2H, t, J=7Hz, —SCH$_2$—), 3.35(3H, s, NCH$_3$), 5.19(1H, broad, OH), 7.23(2H, s, 2×aromatic H). | (C$_{23}$H$_{39}$NO$_3$S) C, 67.44; H, 9.60; N, 3.42; S, 7.83 C, 67.58; H, 9.58; N, 3.52; S, 7.93 |
| 12 | 1.28-1.40(8H, m, 4×CH$_2$), 1.42(18H, s, 2×C(CH$_3$)$_3$), 1.55-1.80(4H, m, 2×CH$_2$), 2.27-2.40(2H, broad, —CH$_2$CO—), 2.82 (2H, t, J=7Hz, —SCH$_2$—), 3.35(3H, s, NCH$_3$), 5.20(1H, broad OH), 7.22(2H, s, 2×aromatic H). | (C$_{24}$H$_{41}$NO$_3$S) C, 68.04; H, 9.76; N, 3.31; S, 7.57 C, 67.89; H, 9.68; N, 3.23; S, 7.48 |
| 13 | 1.22(12H, s, 6×CH$_2$), 1.37(18H, s, 2×(C(CH$_3$)$_3$), 1.53-1.72 (4H, m, 2×CH$_2$), 2.28(2H, broad, —CH$_2$CO—), 2.77(2H, t, J=7Hz, —SCH$_2$—), 3.29(3H, s, NCH$_3$), 5.20(1H, broad, OH), 7.17(2H, s, 2×aromatic H). | (C$_{26}$H$_{45}$NO$_3$S) C, 69.13; H, 10.04; N, 3.10; S, 7.10 C, 68.83; H, 9.92; N, 3.04; S, 6.82 |
| 14 | 1.25(14H, s, 7×CH$_2$), 1.43(18H, s, 2×C(CH$_3$)$_3$), 1.53-1.76(4H, m, 2×CH$_2$), 2.34(2H, broad, —CH$_2$CO—), 2.82 (2H, t, J=7Hz, —SCH$_2$—), 3.35(3H, s, NCH$_3$), 5.18(1H, broad, OH), 7.23(2H, s, 2×aromatic H). | (C$_{27}$H$_{47}$NO$_3$S) C, 69.36; H, 10.17; N, 3.01; S, 6.88 C, 69.50; H, 10.19; N, 3.04; S, 7.09 |

EXAMPLE 15

N-5-(3,5-Di-tert-butyl-4-hydroxyphenylthio)pentyl-acetohydroxamic acid (I15)

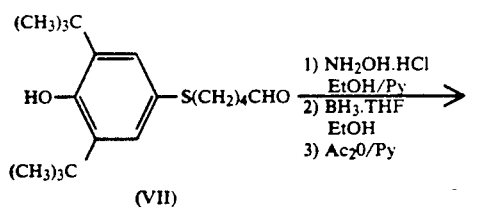

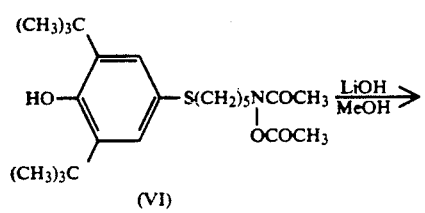

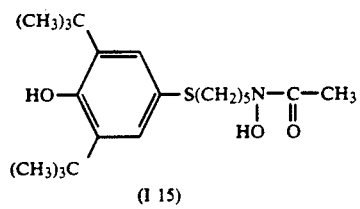

A mixture of 990 mg (3.07 mmol) of 5-(3,5-di-tert-butyl-4-hydroxyphenylthio)valeroaldehyde (VII), 1.0 g (14.4 mmol) of hydroxylamine hydrochloride, and 10 ml of pyridine in 20 ml of ethanol was refluxed for 6 hours under heating and the reaction mixture was concentrated under reduced pressure. To the residue was added 20 ml of a 5% aqueous solution of hydrochloric acid and the mixture extracted with 50 ml of dichloromethane. The organic layer was washed with 50 ml of water twice, dried over anhydrous sodium sulfate, and concentrated under reduced pressure to give 1.01 g of an oily residue. To a solution of the residue in 30 ml of dry tetrahydrofuran was added dropwise 7.3 ml (7.3 mmol) of 1M solution of boran in tetrahydrofuran under ice-cooling and stirring, the mixture was stirred for 4 hours at the same temperature and then 5 ml of a 10% aqueous solution of sodium hydroxide was added dropwise thereto. After addition, the resulting mixture was stirred for 30 minutes at room temperature and the reaction mixture was extracted with 100 ml of dichloromethane. The dichloromethane layer was washed with 100 ml of water twice, dried over anhydrous sodium sulfate, and concentrated under reduced pressure to give a residue as an yellow oil. To a solution of the residue in 20 ml of acetic anhydride was added 10 ml of pyridine and the mixture was allowed to stand for 20 hours at room temperature. The reaction mixture was concentrated under reduced pressure and the residue was chromatographed on silica gel to give 710 mg of aceto N-5-(3,5-di-tert-butyl-4-hydroxyphenylthio)pentyl-acetohydroxamate (VI) as a pale yellow oil in 62% yield from the fraction eluted with ether.

To a solution of 710 mg (1.67 mmol) of the compound (VI) in 20 ml of methanol was added 280 mg (6.67 mmol) of lithium hydroxide and the mixture was stirred for 1 hour at room temperature. The reaction mixture was concentrated under reduced pressure and 20 ml of a 10% aqueous solution of hydrochloric acid was added to the residue under ice-cooling. The mixture was extracted with 50 ml of ether and the ether layer was washed with 50 ml of water twice, dried over anhydrous sodium sulfate, and concentrated under reduced pressure. The residue was chromatographed on silica gel to give the aimed compound (I15) from the fraction eluted with a mixture of ether-ethyl acetate (3:1) and the product was recrystallized from ether-n-hexane (1:1) to give 530 mg of the compound (I15) as colorless needle-like crystals in 83% yield.

mp. 103° C. to 105° C.

Anal. Calcd. (%) for $C_{21}H_{35}NO_3S$: C, 66.10; H, 9.25; N, 3.67; S, 8.40; Found (%): C, 65.90; H, 9.16; N, 3.65; S, 8.37; IR $\nu$max (Nujol) cm$^{-1}$: 3600, 3105, 2630(OH), 1575, 1520(CO). 200 MHz NMR (CDCl$_3$) $\delta$: 1.38–1.53(2H, m, CH$_2$), 1.43(18H, s, 2×C(CH$_3$)$_3$), 1.60–1.80(4H, m, 2×CH$_2$), 2.09(3H, s, COCH$_3$), 2.84(2H, t, J=7 Hz, —SCH$_2$—), 3.61(2H, t, J=7 Hz, —NCH$_2$—), 5.21(1H, s, —OH), 7.23(2H, s, 2×aromatic H).

EXAMPLE 16

N-5-[(3,5-di-tert-butyl-4-hydroxyphenylthio)pentyl]isobutyrohydroxamic acid (I16)

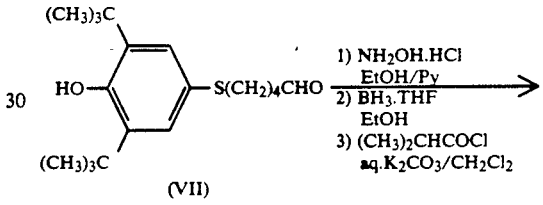

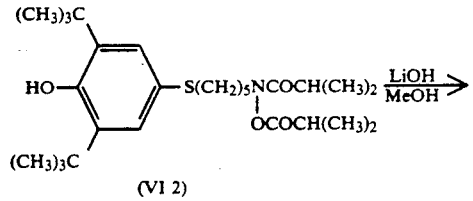

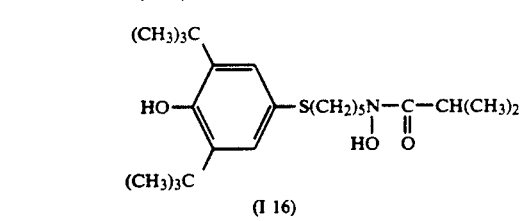

According to the procedure shown in Example 15, 990 mg (3.07 mmol) of 5-(3,5-di-tert-butyl-4-hydroxyphenylthio)valeroaldehyde (VII) was allowed to react with 1.0 g (14.4 mmol) of hydroxylamine hydrochloride in 20 ml of ethanol in the presence of 10 ml of pyridine to give an oxime intermediate of which solution in 30 ml of dry tetrahydrofuran was reduced by 7.3 ml (7.3 mmol) of 1M solution of boran in tetrahydrofuran to give the crude 5-(3,5-di-tert-butyl-4-hydroxyphenylthio)pentylhydroxylamine as a pale yellow oil. To a solution of the oil in 20 ml of dichloromethane was added 10 ml of aqueous solution of 690 mg (5 mmol) of potassium carbonate and to the resulting mixture was added dropwise a solution of 640 mg (6 mmol) of isobutyryl chloride under ice-cooling and viogorously stirring. After addition, the mixture was stirred for 30 minutes at the same temperature, the dichloromethane layer was separated, washed with 50 ml of water twice, dried over anhydrous sodium sulfate, and concentrated under reduced pressure. The residue was chromatographed to give 417 mg of isobutyl N-5-(3,5-di-tert-butyl-4-hydroxyphenylthio)pentylisobutyrylhydroxamic acid (VI2) as a pale yellow oil in 28.3% yield.

To a solution of 417 mg of the compound (VI2) in 15 ml of methanol was added 250 mg (6 mmol) of lithium hydroxide and the mixture was stirred for 1 hour at room temperature. The reaction mixture was concentrated under reduced pressure. The product which was prepared by treating the residue according to the procedure shown Example 15 was chromatographed to give the aimed compound (I16) from the fraction eluted with a mixture of ether-n-hexane (1:1). The aimed compound (I16) was recrystallized from n-pentane to give 295 mg of prismatic crystals in 82.8% yield.

mp. 109° C. to 111° C.

Anal. Calcd. (%) for $C_{23}H_{39}NO_3S$: C, 67.44; H, 9.60; N, 3.42; S, 7.83; Found (%): C, 67.18; H, 9.62; N, 3.36; S, 7.78. IR $\nu$max (Nujol) cm$^{-1}$: 3590, 3120(OH), 1622, 1605(CO). 200 MHz NMR(CDCl$_3$) $\delta$: 1.11(6H, d, J=7 Hz, 2×CH$_3$), 1.37(18H, s, 2×C(CH$_3$)$_3$), 1.40–1.47(2H, m, CH$_2$), 1.53–1.72(4H, m, 2×CH$_2$), 2.72(1H, broad, CH), 2.78(2H, t, J=7 Hz, —SCH$_2$—), 3.58(2H, t, J=7 Hz, —NCH$_2$—), 5.26(1H, broad, —OH), 7.17(2H, s, 2×aromatic H).

EXAMPLE 17

N-5-[(3,5-di-tert-butyl-4-hydroxyphenylthio)pentyl]-benzohydroxamic acid (I17)

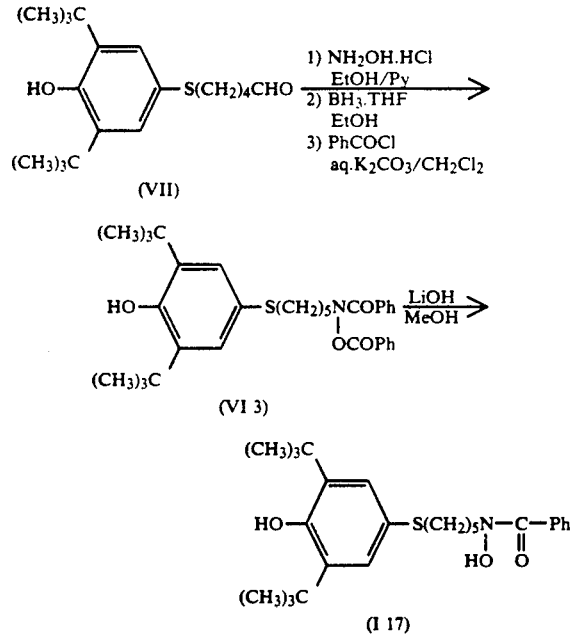

(I 17)

According to the procedure shown in Example 15, a mixture of 968 mg (3.0 mmol) of the compound (VII), 1.0 g (14.4 mmol) of hydroxylamine hydrochloride, and 10 ml of pyridine in 20 ml of ethanol was refluxed under heating to give the oxime which was treated with 7 ml (7 mmol) of 1M solution of boran in tetrahydrofuran to give the crude N-5-(3,5-di-tert-butyl-4-hydroxyphenylthio)pentylhydroxylamine. To a solution of the crude compound in 20 ml of dichloromethane was added 10 ml of an aqueous solution of 690 mg (5 mmol) of potassium carbonate and the mixture was stirred vigorously. The product was chromatographed on silica gel to give 411 mg of benzoyl N-5-(3,5-di-tert-butyl-4hydroxyphenylthio)pentyl-benzoylhydroxamate (VI3) as a colorless oil in 25% yield from the fraction eluted with a mixture of ether-n-hexane (1:1). According to the procedure shown in Example 15, 411 mg (0.75 mmol) of the compound (VI3) was treated with 250 mg (6 mmol) of lithium hydroxide in 15 ml of methanol and the resulting product was chromatographed on silica gel to give the aimed compound (I17) from the fraction eluted with a mixture ether-n-hexane (1:1). The compound (I17) was recrystallized from n-pentane containing small amount of ether to give 205 mg of the compound as colorless needle-like crystals.

mp. 67° C. to 69° C.

Anal. Calcd. (%) for $C_{26}H_{37}NO_3S$: C, 70.39; H, 8.41; N, 3.16; S, 7.23; Found (%): C, 70.26; H, 8.40; N, 3.34; S, 7.05. IR $\nu$max (Nujol) cm$^{-1}$: 3640, 3120sh(OH), 1610, 1600(CO). 200 MHz NMR(CDCl$_3$)$\delta$: 1.30–1.47(2H, m, CH$_2$), 1.42(18H, s, 2×C(CH$_3$)$_3$), 1.50–1.82(4H, m, 2×CH$_2$), 2.79(2H, t, J=7 Hz, —SCH$_2$—), 3.64(2H, t, J=7 Hz, —NCH$_2$—), 5.20(1H, broad, —OH), 7.21(2H, s, 2×aromatic H), 7.40–7.55(5H, m, 5×aromatic H).

EXAMPLE 18

N-Benzyl-5-(3,5-di-tert-butyl-4-hydroxyphenylthio)-valerohydroxamic acid (I18)

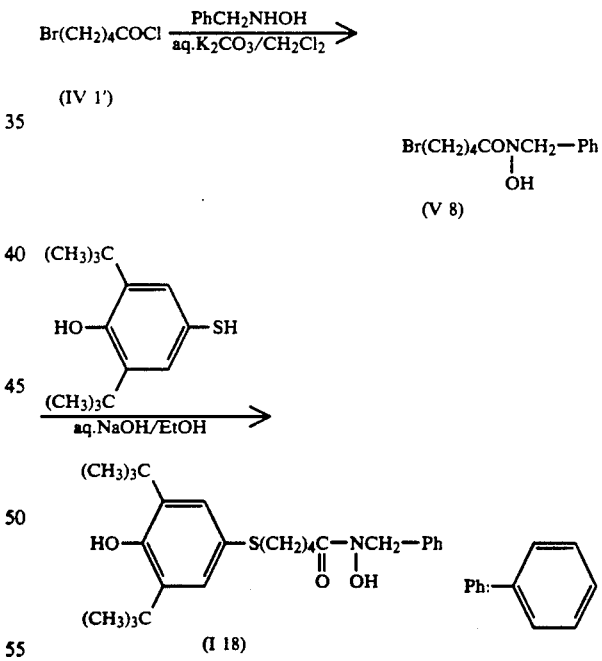

(I 18)

According to the procedure shown in Example 8, 724 mg (4 mmol) of 5-bromovaleric acid (IV1) was treated with about 1 ml of thionyl chloride to give the compound (IV1') which was allowed to react with 493 mg (4 mmol) of N-benzylhydroxylamine in the presence of 560 mg (4 mmol) of patassium carbonate to give crude N-benzyl 5-bromovalerohydroxamic acid (V8) as a pale yellow oil. Without further purification, the crude product was added to 10 ml of a solution of 960 mg (4 mmol) of 3,5-di-tert-butyl-4-hydroxythiophenol in ethanol and then 5 ml of an aqueous solution of 320 mg (8 mmol) of sodium hydroxide was added thereto. The mixture was stirred for 5 hours at room temperature. To the reaction mixture was added 20 ml of a 5% aqueous solution of hydrochloric acid under ice-cooling and the mixture was extracted with 50 ml of dichloromethane. The organic layer was washed with 50 ml of water twice, dried over anhydrous sodium sulfate, and concentrated under reduced pressure to give a crystalline residue which was recrystallized from a mixture of ether- methanol (10:1) to give 1.31 g of the aimed compound (I18) as colorless laminar crystals in 73.8% yield.

The physical data are shown in Table 4.

EXAMPLE 19

N-2-(Phenyl)ethyl 5-(3,5-di-tert-butyl-4-hydroxyphenyl)thiovalerohydroxamic acid (I19)

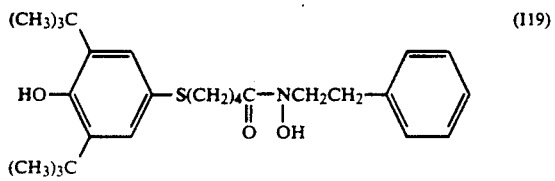

procedure shown in Example 8 except that 6-bromocapric acid was used instead of 5-bromovaleric acid.

The physical data are shown in Table 4.

EXAMPLE 21

N-2-(Phenyl)ethyl 6-(3,5-di-tert-butyl-4-hydroxyphenylthio)caprohydroxamic acid (I21)

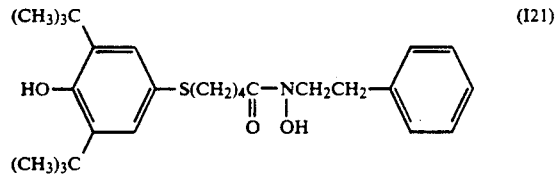

The aimed compound (I21) was prepared according to the precedure shown in Example 8 except that 6-bromocapric acid was used instead of 5-bromovaleric acid and that N-2-(phenyl)ethylhydroxylamine was used instead of N-benzyl hydroxylamine. The product was recrystallized from a mixture of ether-n-hexane to give colorless needle like crystals in 78.4% yield.

The physical data are shown in Table 4.

TABLE 4

| Ex. No. | mp. [°C.] | IRν max [cm$^{-1}$] (Nujol) | NMR δ ppm(CDCl$_3$) | Analysis (Molecura Formula) Calcd. (%): Found (%): |
|---|---|---|---|---|
| 18 | 143–145 | 3580, 3210, 1615, 1600 | 1.42(18H, s, 2×C(CH$_3$)$_3$), 1.60–1.90(4H, m, 2×CH$_2$), 2.42(2H, broad, —CH$_2$CO—), 2.83(2H, t, J=7Hz, —SCH$_2$—), 4.82(2H, s, —C$H_2$—Ph), 5.20(1H, s, —OH), 7.22(2H, s, 2×aromatic H), 7.29–7.38(5H, m, 5×aromatic H). | (C$_{26}$H$_{37}$NO$_3$S) C, 70.39; H, 8.41; N, 3.16; S, 7.23; C, 70.17; H, 8.46; N, 3.12; S, 7.29. |
| 19 | 75–76 | 3640, 3620, 3160, 1620, 1602 | 1.43(18H, s, 2×C(CH$_3$)$_3$), 1.46(4H, broad, 2×—CH$_2$—), 1.83(2H, broad, —C$H_2$Ph), 2.70(2H, broad, —CH$_2$CO—), 2.98(2H, t, J=7Hz, —SCH$_2$—), 3.84(2H, t, J=6Hz, N—CH$_2$—), 5.23(1H, broad, —OH), 7.14–7.31(5H, m, 5×aromatic H), 7.20(2H, s, 2×aromatic H). | (C$_{27}$H$_{39}$NO$_3$S) C, 70.86; H, 8.59; N, 3.06; S, 7.01; C, 70.86; H, 8.54; N, 3.30; S, 6.84. |
| 20 | 107–109 | 3580, 3190, 1610(sh), 1595. | 1.17–1.39(2H, m, —CH$_2$—), 1.43(18H, s, 2×C(CH$_3$)$_3$), 1.59–1.80(4H, 2×—CH$_2$—), 2.41(1H, broad, —C$H_2$CO), 2.81 (2H, t, J=7Hz, —SCH$_2$—), 4.82(2H, s, —C$H_2$Ph), 5.22(1H, broad, —OH), 7.22(2H, s, 2×aromatic H), 7.29–7.37(5H, m, 5×aromatic H). | (C$_{27}$H$_{39}$NO$_3$S) C, 70.86; H, 8.59; N, 3.06; S, 7.01; C, 70.81; H, 8.63; N, 3.02; S, 6.90. |
| 21 | 87–89 | 3600, 3160, 1627, 1600. | 1.41(18H, s, 2×C(CH$_3$)$_3$), 1.30–1.65(6H, m, 3×—CH$_2$—), 2.41(2H, t, J=7Hz, CH$_2$CO), 2.76(2H, t, J=7Hz, C$H_2$—Ph), 2.89 (2H, t, J=7Hz, —SCH$_2$—), 3.80(2H, t, J=7Hz, —NCH$_2$—), 7.20–7.35(7H, m, 7 × aromatic H). | (C$_{28}$H$_{41}$NO$_3$S) C, 71.30; H, 8.76; N, 2.97; S, 6.80; C, 71.28; H, 8.80; N, 3.11; S, 6.83. |

The aimed compound (I19) was prepared according to the procedure shown in Example 18 except that N-2-(phenyl)ethyl hydroxylamine was used instead of N-benzylhydroxylamine. The compound was recrystallized from a mixture ether-n-hexane (1:1) to give colorless prismatic crystals in 70.5% yield.

The physical data are shown in Table 4.

EXAMPLE 20

N-Benzyl 6-(3,5-di-tert-butyl-4-hydroxyphenyl)thiocaprohydroxamic acid (I20)

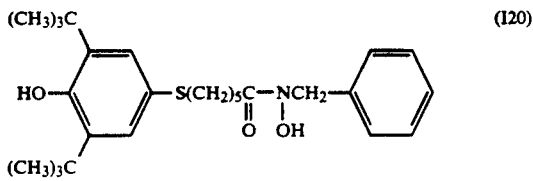

The aimed compound (I20) was prepared in 76.5% yield as colorless prismatic crystals according to the

TEST EXAMPLE 1

Suppression on Production of Peroxidized Lipids in a Homogenate of Rat Brain:

SD strain rats (body weight, about 200 g) were sacrificed by cutting down their heads, and the brains were taken out. The brains were homogenated with a 4-fold amount of 0.05M phosphate-sodium chloride buffer (pH 7.4) and centrifuged at 1,000×g for 10 minutes. The supernatant was kept at −80° C. for storage.

The supernatant was diluted with a 2-fold amount of the same phosphate-sodium chloride buffer as above, and 0.45 ml of the dilution was combined with 30 μl of ethanol per se (vehicle) or ethanol solution contaning a test compound, followed by incubation at 37° C. for 30 minutes. The reaction was terminated by addition of a solution of 0.1% butylhydroxytoluene (BHT) (20 μl) in 25% metaphosphoric acid (125 μl). After deproteinization, the peroxidized lipids in the supernatant were measured by the thiobarbituric acid (TBA) method according to the description by Ohkawa et al.: in Anal. Biochem., Vol. 95, page 351 (1979). The amount of peroxidized lipids produced was compared with that in the vehicle applied group and expressed in % control. The results are shown in Table 5.

TABLE 5

Suppression on Production of Peroxidized Lipids in a Homogenate of Rat Brain:

| Test Compd. No. | Test Compd. Final Concentration (mM) | Peroxidized Lipids Produced (% to Control) |
| --- | --- | --- |
| I 1 | 0.001 | 71.9 |
|  | 0.01 | 0 |
|  | 0.1 | 0 |
| I 2 | 0.001 | 42.0 |
|  | 0.01 | 0 |
|  | 0.1 | 0 |
| I 3 | 0.001 | 44.2 |
|  | 0.01 | 0 |
|  | 0.1 | 0 |
| I 4 | 0.001 | 28.6 |
|  | 0.01 | 0 |
|  | 0.1 | 0 |
| I 5 | 0.0001 | 99.0 |
|  | 0.001 | 37.4 |
|  | 0.01 | 0 |
|  | 0.1 | 0 |
| I 6 | 0.001 | 37.2 |
|  | 0.01 | 0 |
|  | 0.1 | 0 |
| I 7 | 0.0001 | 99.0 |
|  | 0.001 | 63.6 |
|  | 0.01 | 0 |
|  | 0.1 | 0 |
| I 8 | 0.0001 | 102.0 |
|  | 0.001 | 1.5 |
|  | 0.01 | 2.5 |
|  | 0.1 | 0 |
| I 9 | 0.0001 | 97.0 |
|  | 0.001 | 5.1 |
|  | 0.01 | 0 |
|  | 0.1 | 0 |
| I 10 | 0.0001 | 94.2 |
|  | 0.001 | 57.4 |
|  | 0.01 | 1.6 |
|  | 0.1 | 1.6 |
| I 11 | 0.0001 | 97.4 |
|  | 0.001 | 46.4 |
|  | 0.01 | 0 |
|  | 0.1 | 0 |
| I 12 | 0.0001 | 94.5 |
|  | 0.001 | 56.6 |
|  | 0.01 | 0 |
|  | 0.1 | 1.3 |
| I 13 | 0.0001 | 93.3 |
|  | 0.001 | 55.4 |
|  | 0.01 | 0 |
|  | 0.1 | 0 |
| I 14 | 0.0001 | 95.3 |
|  | 0.001 | 60.3 |
|  | 0.01 | 0 |
|  | 0.1 | 0 |
| I 15 | 0.0001 | 97.3 |
|  | 0.001 | 78.8 |
|  | 0.01 | 1.6 |
|  | 0.1 | 0 |
| I 16 | 0.001 | 89.5 |
|  | 0.01 | 2.2 |
|  | 0.1 | 0.3 |

TABLE 5-continued

Suppression on Production of Peroxidized Lipids in a Homogenate of Rat Brain:

| Test Compd. No. | Test Compd. Final Concentration (mM) | Peroxidized Lipids Produced (% to Control) |
| --- | --- | --- |
| I 17 | 0.001 | 77.6 |
|  | 0.01 | 1.1 |
|  | 0.1 | 0 |
| I 18 | 0.001 | 84.9 |
|  | 0.01 | 2.4 |
|  | 0.1 | 1.1 |
| I 19 | 0.001 | 81.6 |
|  | 0.01 | 13.5 |
|  | 0.1 | 0 |
| I 20 | 0.001 | 81.9 |
|  | 0.01 | 1.1 |
|  | 0.1 | 0.3 |
| I 21 | 0.001 | 86.8 |
|  | 0.01 | 1.4 |
|  | 0.1 | 0 |
| Reference Compound | 0.001 | 81.9 |
|  | 0.001 | 102.4 |
|  | 0.01 | 58.3 |
|  | 0.1 | 27.8 |

Reference Compound: Probucol

It is understood from the above results, the compounds of this invention show an excellent anti-oxidation activity to lipids. And they thereby prevent the incorporation of LDL into macrophages by inhibiting the denaturation of LDL.

It can be expected that the compounds of this invention inhibit the formation of atheroma in the early stage of arteriosclerosis and that arrest the progression of arteriosclerosis.

What we claimed is:

1. A compound of the formula

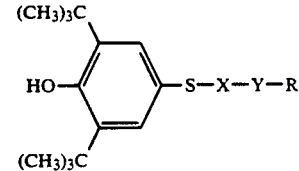

wherein X is straight $C_4$ or $C_5$ alkylene; Y is CO—N-(OH); and R is hydrogen, methyl, heptyl or cyclohexyl; or a pharmaceutically acceptable salt thereof.

2. The compound claimed in claim 1, which is N-methyl-5-(3,5-di-tert-butyl-4-hydroxyphenyl)thiovalerohydroxamic acid.

3. The compound claimed in claim 1, which is 5-(3,5-di-tert-butyl-4-hydroxyphenyl)thiovalerohydroxamic acid.

4. The compound claimed in claim 1, which is N-methyl-6-(3,5-di-tert-butyl-4-hydroxyphenyl)thiocaprohydroxamic acid.

5. The compound claimed in claim 1, which is N-n-Heptyl-5-(3,5-di-tert-butyl-4-hydroxyphenyl)thiovalerohydroxamic acid.

6. The compound claimed in claim 1, which is N-Cyclohexyl-5-(3,5-di-tert-butyl-4-hydroxyphenyl)thiovalerohydroxamic acid.

* * * * *